United States Patent
Perreault et al.

(10) Patent No.: US 7,316,147 B2
(45) Date of Patent: Jan. 8, 2008

(54) APPARATUSES FOR CRIMPING AND LOADING OF INTRALUMINAL MEDICAL DEVICES

(75) Inventors: Daniel Perreault, Ham Lake, MN (US); Mark Edin, Minneapolis, MN (US); Bruce Asmus, Minnetonka, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 345 days.

(21) Appl. No.: 10/767,985

(22) Filed: Jan. 29, 2004

(65) Prior Publication Data
US 2005/0166389 A1  Aug. 4, 2005

(51) Int. Cl.
*B21J 7/16* (2006.01)

(52) U.S. Cl. .................. 72/402; 29/283.5; 29/508; 29/516

(58) Field of Classification Search .......... 29/508, 29/515, 516, 283.5; 72/402; 606/108; 623/1.11
See application file for complete search history.

(56) References Cited

U.S. PATENT DOCUMENTS

| | | | |
|---|---|---|---|
| 1,968,456 A * | 7/1934 | Kliefoth | 181/294 |
| 3,695,087 A | 10/1972 | Tuberman | 72/402 |
| 4,567,650 A | 2/1986 | Balyasny et al. | 29/822 |
| 5,243,846 A | 9/1993 | Davis et al. | 72/402 |
| 5,261,263 A | 11/1993 | Whitesell | 72/410 |
| 5,715,723 A | 2/1998 | Owens | 72/402 |
| 5,725,519 A | 3/1998 | Penner et al. | 606/1 |
| 5,738,674 A | 4/1998 | Williams et al. | 606/1 |
| 5,752,405 A | 5/1998 | Gerst et al. | 72/312 |
| 5,810,873 A | 9/1998 | Morales | 606/198 |
| 5,836,952 A | 11/1998 | Davis et al. | 606/108 |
| 5,920,975 A | 7/1999 | Morales | 29/282 |
| 5,931,851 A | 8/1999 | Morales | 606/194 |
| 6,009,614 A | 1/2000 | Morales | |
| 6,018,857 A | 2/2000 | Duffy et al. | 29/407.01 |
| 6,051,002 A | 4/2000 | Morales | 606/108 |
| 6,063,102 A | 5/2000 | Morales | 606/198 |
| 6,074,381 A | 6/2000 | Dinh et al. | 606/1 |
| 6,082,990 A | 7/2000 | Jackson et al. | 425/517 |
| 6,108,886 A | 8/2000 | Kimes et al. | 29/280 |
| 6,125,523 A | 10/2000 | Brown et al. | 29/519 |
| 6,141,855 A | 11/2000 | Morales | 29/516 |
| 6,167,605 B1 | 1/2001 | Morales | 29/282 |
| 6,171,234 B1 * | 1/2001 | White et al. | 600/102 |
| 6,202,272 B1 | 3/2001 | Jackson | 29/235 |
| 6,240,615 B1 | 6/2001 | Kimes et al. | 29/516 |
| 6,306,141 B1 | 10/2001 | Jervis | 606/78 |
| 6,309,383 B1 | 10/2001 | Campbell et al. | 606/1 |

(Continued)

OTHER PUBLICATIONS

U.S. Appl. No. 10/788,088, filed Feb. 26, 2004, Jan Weber and Tracee Eidenschink.

*Primary Examiner*—Jermie E. Cozart
(74) *Attorney, Agent, or Firm*—Vidas, Arrett & Steinkraus, P.A.

(57) ABSTRACT

Crimping apparatuses for reducing the diameter of an intraluminal medical device from a first diameter to a second diameter prior to loading the medical device into a catheter delivery system and loading apparatuses for introducing the medical device into a catheter delivery system, the devices constructed and arranged for matingly engaging one another, combinations thereof, and methods of using the devices.

38 Claims, 6 Drawing Sheets

U.S. PATENT DOCUMENTS

| | | | |
|---|---|---|---|
| 6,352,547 B1 | 3/2002 | Brown et al. | 606/198 |
| 6,360,577 B2 | 3/2002 | Austin | 72/402 |
| 6,387,117 B1 | 5/2002 | Arnold, Jr. et al. | 623/1.1 |
| 6,510,722 B1 | 1/2003 | Ching et al. | 72/402 |
| 6,568,235 B1 | 5/2003 | Kokish | 72/402 |
| 6,629,350 B2 | 10/2003 | Motsenbocker | 29/283.5 |
| 6,651,478 B1 | 11/2003 | Kokish | 72/402 |
| 2002/0035774 A1 | 3/2002 | Austin | 29/516 |
| 2002/0116045 A1 | 8/2002 | Eidenschink | 623/1.11 |
| 2002/0138966 A1 | 10/2002 | Motsenbocker | 29/516 |
| 2002/0163104 A1 | 11/2002 | Motsenbocker | 264/320 |
| 2003/0192164 A1 | 10/2003 | Austin | 29/505 |
| 2004/0199239 A1* | 10/2004 | Austin et al. | 623/1.11 |

\* cited by examiner

APPARATUSES FOR CRIMPING AND LOADING OF INTRALUMINAL MEDICAL DEVICES

BACKGROUND OF THE INVENTION

This invention relates to an apparatus and methods for reducing in size an intraluminal medical device such as a stent, stent-graft, graft, or vena cava filter, and for introducing the medical device into the distal end of a delivery system for delivery of the medical device into the vasculature of a patient.

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Stents are available in both self-expanding and inflation expandable configurations. Inflation expandable stents are well known and widely available in a variety of designs and configurations. Both self-expanding and inflation expandable stents are typically crimped to their reduced configuration after being disposed about a delivery catheter. They are maneuvered to the deployment site and expanded to the vessel diameter either by fluid inflation of a balloon positioned between the stent and the delivery catheter, or upon release of the self-expanding stent from its crimped state, typically from a retaining sleeve or delivery sheath.

A number of techniques for crimping a stent to a balloon are used. One such technique that is commonly used in the radiological suite involves hand crimping the stent to the balloon. A stent is placed over an uninflated balloon and then squeezed with the fingers until the stent is in intimate contact with the uninflated balloon. The technique is highly operator dependent and can affect stent profile and stent placement with respect to the balloon and radiopaque markers. It can also affect the dilatation length of the stent and lead to pinching of the balloon.

Typically, mechanical stent crimping devices are either used to crimp the stent to the catheter prior to shipping the stent or in the radiological suite. In the latter case, the radiologist selects a bare stent with the desired properties and then mechanically crimps the stent to the desired balloon catheter.

Crimping and loading of self-expanding stents is often a more complicated procedure. Self-expanding stents are typically loaded into a constraining structure of a catheter delivery device after crimping of the stent. Stent loading typically involves pushing or pulling the stent out of a device in a constricted state and directly into a stent delivery system, or into an intermediary region and then into the delivery system. Alignment of the delivery system, typically the distal end of a catheter delivery device, with the crimping device can be problematic because the stent is relatively fragile, and typically the constrained outer diameter of the stent is only slightly less than the available inner diameter of the receiving delivery system or intermediate station. If the delivery system is not properly aligned with the crimping device, the stent and/or the catheter delivery system can be damaged. The constraining structure for the stent is typically a retaining sleeve or delivery sheath and is often in a tubular form. Damage may involve flaring of the ends of the catheter delivery system, or peeling or rolling of the tubing onto itself.

Thus, there is a continuing need for improved devices and methods for loading a stent onto a delivery system such as a balloon catheter that are simpler, less expensive, more convenient, more reliable and avoid damage to the stent.

SUMMARY OF THE INVENTION

The present invention relates generally to an apparatus and method for reducing an intraluminal medical device in size, and for introducing the medical device into the distal end of a catheter delivery assembly. Suitable medical devices include stents, stent-grafts, grafts and vena cava filters whether self-expandable or balloon expandable.

In one aspect, the present invention relates to an apparatus for reducing in size an intraluminal medical device, the apparatus constructed and arranged for matingly engaging an apparatus for introducing the medical device into the distal end of a catheter delivery assembly.

Any crimping configuration may be employed herein. Typically, such apparatuses are designed for applying relatively uniform radially inward forces to the medical device. The apparatus reduces the size of the medical device from a first diameter to a second diameter. Some such apparatuses have a plurality of coupled movable blades disposed about a reference circle to form an aperture whose size may be varied.

In another aspect, the present invention relates to an apparatus for introducing an intraluminal medical device into the distal end of a catheter delivery assembly, the apparatus constructed and arranged to matingly engage an apparatus for reducing a medical device from a first diameter to a second diameter.

In one embodiment, the introducing apparatus includes a hollow cylindrical housing, referred to hereinafter as an introducer shaft, which is designed for receiving the medical device. The hollow introducer shaft is further equipped with a hollow plug which tapers from one end having a larger opening to the other end having a smaller opening. The plug is insertable into the hollow cylindrical housing. The plug tapers from one end which has a larger opening, the larger opening being located at the end of the housing into which the medical device is fed, to a smaller end, the smaller end engaging the distal end of a catheter delivery assembly.

The plug may be of a variety of configurations. In one embodiment, the plug has conical flanges extending from the end closest the catheter delivery assembly. The conical flanges may be designed such that they more easily engage the outer catheter shaft.

In another embodiment, the plug has straight edges.

In one embodiment, the introducer shaft has an external triangular form which fits into a lumen of the introducer apparatus. This allows for air to flow around the sides of the housing through the lumen.

The present invention also relates to combinations of the above-described apparatuses.

In one embodiment, the apparatus for reducing the medical device in size includes at least three coupled, movable blades disposed about a reference circle to form an aperture whose size may be varied. The apparatus further includes at least one alignment tool connected to at least one blade. The at least one alignment tool may be integral with or modular with the at least one blade.

In another embodiment, each blade has an alignment tool such that a closed alignment shape is formed with the motion of the blades. The alignment tools may either be an integral part of each of the blades, or may be modular with the blades. The latter case allows for different alignment shapes to be incorporated depending on particular application for which the aperture is being used.

As used herein, the term "integral" when used in reference to an alignment tool being integral with a blade shall refer to those alignment tools which are formed as part of the blades themselves, or are secured such that they are not readily removable from the blades.

As used herein, the term "modular" when used in reference to an alignment tool being integral with a blade shall refer to those alignment tools which are readily removable from the blades.

Furthermore, the alignment tools may be designed such that they form a continuous alignment shape around the aperture, or they can be designed to allow for spacing between the blades which form the aperture. The latter case may be employed for use with a sheath or sleeve mechanism, for example, or to gain access to the tip of the crimped medical device with the delivery system already in place.

The alignment tool according to the present invention may of course be employed with any apparatus which is employed to uniformly reduce the size of a medical device. These devices are often referred to as crimpers or crimping devices. Such devices are described, for example, in commonly assigned U.S. Pat. No. 6,360,577, in U.S. Provisional Patent Application Publication No. US 2002/0138966 A1 and in copending U.S. patent application Ser. No. 10/826, 035, for example, each of which is incorporated by reference herein in its entirety.

The present invention also relates to methods of using the apparatuses described herein. In one embodiment, the present invention relates to a method of crimping and loading a medical device into a catheter delivery device, the method including the steps of providing a crimping apparatus having an actuation hub for matingly engaging a loading apparatus, placing the medical device into the crimping apparatus, applying a radial inward force while the medical device is in the crimping apparatus such that the diameter of said medical device is reduced from a first diameter to a second diameter, providing a loading apparatus having a plug for matingly engaging said crimping apparatus, mating the crimping apparatus and the loading apparatus and transporting the medical device from the crimping apparatus to the loading apparatus, the steps not necessarily in that order.

The present invention, in at least some of its embodiments, therefore provides for improved alignment of the medical device with the aperture of the crimping tool thereby alleviating the need for calibration or for external alignment efforts to the aperture axis. Furthermore, at least some of the apparatuses as described herein, reduce the risk of damage to the intraluminal medical device and/or the catheter delivery assembly during transition from the crimping apparatus to the introducer apparatus.

Other benefits and advantages and will become apparent from the following description.

All patents discussed herein are incorporated by reference herein in their entirety.

DETAILED DESCRIPTIONS OF THE INVENTION

While this invention may be embodied in many different forms, there are described in detail herein specific embodiments of the invention. This description is an exemplification of the principles of the invention and is not intended to limit the invention to the particular embodiments illustrated.

Figure 1:
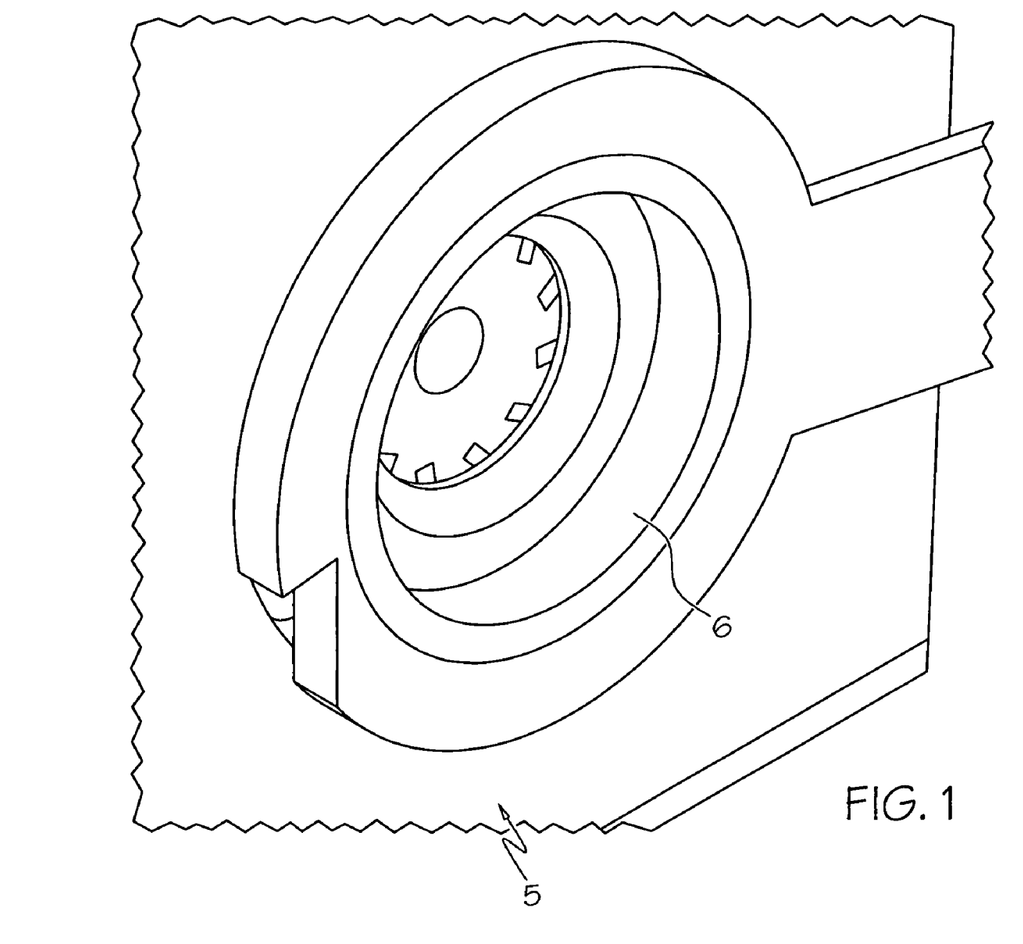
FIG. 1 illustrates an actuation hub for use with any crimping apparatus according to the present invention.

Turning now to the figures, FIG. 1 illustrates generally at 5, an internally tapered actuation hub which may be used in combination with any crimping device. As used herein, the term "crimping" shall refer to a reduction in size or profile of the medical device, i.e. the diameter of a stent, for example. The actuation hub 5 is employed for matingly engaging a loading assembly for introducing an intraluminal medical device into a catheter delivery assembly. The intraluminal device is typically introduced when its in a reduced size.

Figure 2:
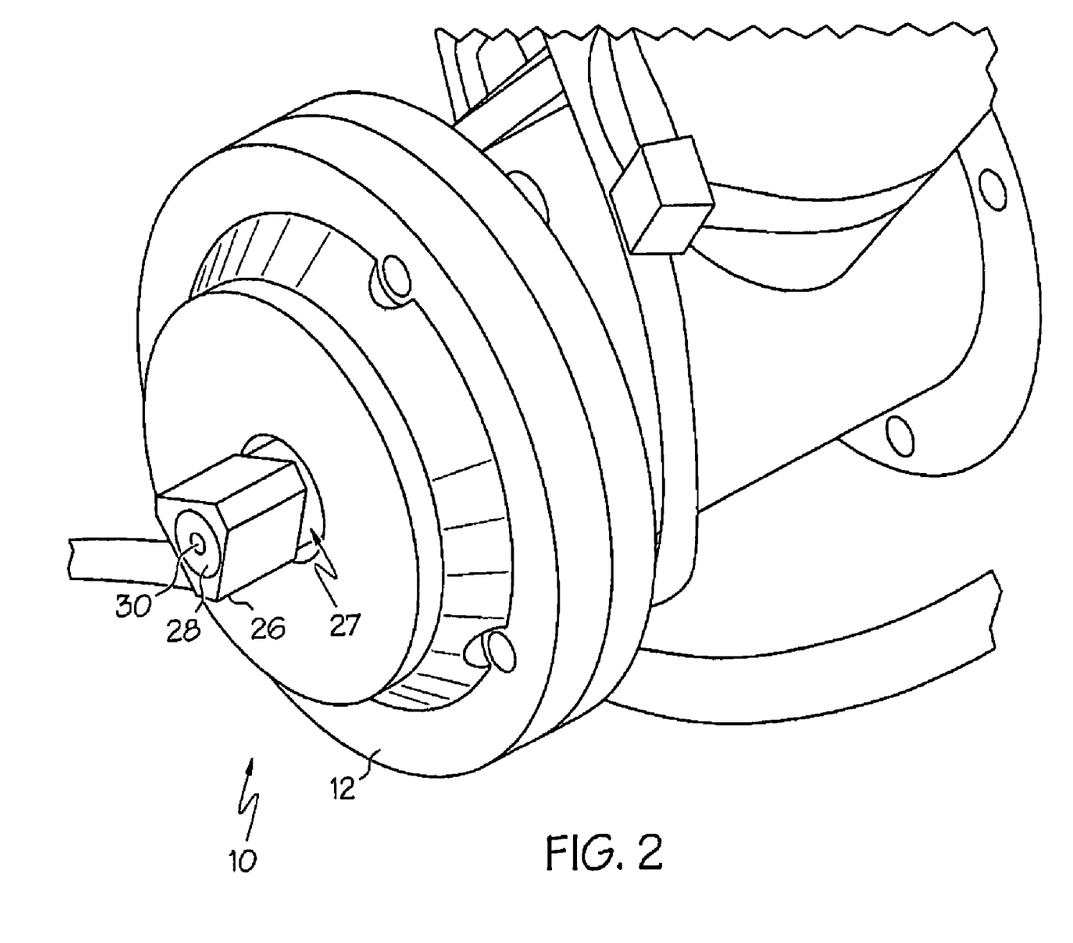
FIG. 2 illustrates an introducer plug for a stent loading assembly according to the present invention.

The tapered actuation hub 6 may be employed to matingly engage a counterpart plug on a stent loading assembly such as that shown generally at 10 in FIG. 2. Plug 10 is shown with an externally tapered head 12. Shown in FIG. 2 is also an introducer shaft 26 which is disclosed in more detail in FIG. 3 below. The stent introducer shaft 26 is further equipped with a stent introducer plug 28 which is also disclosed in more detail in FIG. 3 below.

The actuation hub 5 may be employed in combination with any type of crimping device. Examples of such devices are found in U.S. Pat. No. 6,360,577, U.S. Patent Application Publication No. 2002/0138966 A1, U.S. Pat. No. 6,568, 235 B1, each of which is incorporated by reference herein in its entirety.

Figure 3:
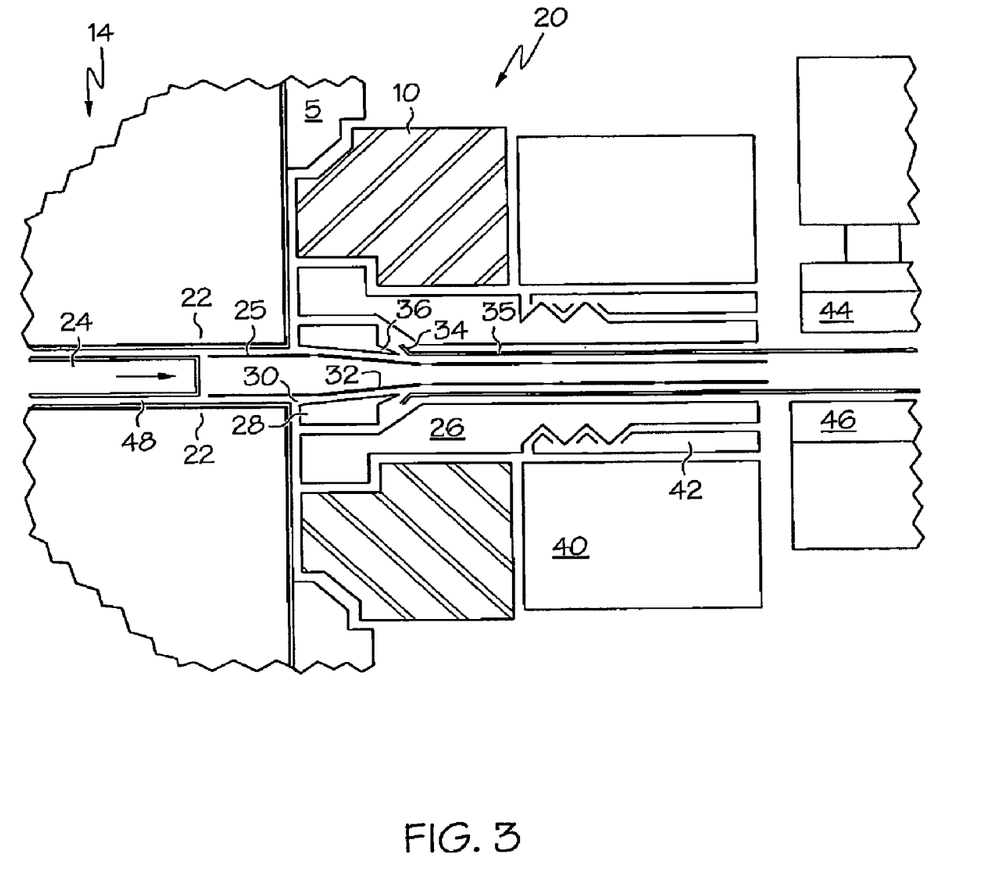
FIG. 3 is a schematic side view of a self-aligning loading assembly according to the present invention.

FIG. 3 schematically illustrates generally at 20, an embodiment of an intraluminal medical device loading assembly or introducer assembly in accordance with the present application in which an actuation hub 5 of a crimping device which may be any crimping device, is shown matingly engaged with the loading assembly 20 using a plug 10 as shown in FIG. 2. Stent 25 is shown partially within the aperture 48 of a crimping device 14 and between crimping blades 22.

A pushing quill 24 is behind stent 25 and moving stent into introducer shaft 26 of stent loading assembly 20. Within introducer shaft 26 is what may be referred to as a stent introducer plug 28. Pushing quill 24 may be actuated pneumatically or mechanically. Stent introducer plug 28 is shown with a tapering lumen. As can be seen from FIG. 3, the diameter of the opening of the introducer plug 28 is slightly larger than the diameter of the aperture 48 of the crimping apparatus 14. The diameter of the opening of the introducer plug 28 adjacent the catheter shaft 35 is slightly larger than the diameter of the opening of the catheter shaft 35. Catheter shaft 35 is shown having a flared end 34. The flared tip may be trimmed off after the stent has been loaded and the crimping/loading procedure is complete. Stent introducer plug 28 is shown in this embodiment with flanged ends 36 which are constructed and arranged in this embodiment to easily engage the flared end of the outer catheter shaft 35. However, stent introducer plug 28 as well as the distal end 34 of catheter shaft 35 may also be provided without the flare and may, for example, be configured with a flat edge as well.

Having a tapered introducer plug 28 as such, allows for the diameter of the intraluminal medical device 32 to be decreased more prior to loading into the shaft of the catheter delivery assembly. Furthermore, the internal taper of the bore extending through introducer plug 28 may be designed such that the bore is slightly larger in diameter than the aperture 48 of a crimping apparatus 14 at the end of the bore closest to the crimping apparatus, which is explained in more detail below, and is slightly smaller in diameter than the diameter of the distal end of the outer catheter shaft of the catheter delivery assembly.

Stent introducer plug 28, having a lumen 30 with an internally tapered surface, may be removable from stent introducer shaft 26 and interchangeable such that the size and configuration may be varied depending on the medical device which is to be introduced into the outer catheter shaft. Furthermore, the stent introducer shaft 26 may also be removable from the stent loading assembly 20.

The length of the introducer plug 28 can be advantageously controlled to be about the same as or just slightly less than the length of a stent strut. During at least one portion of stent loading, one strut is in the introducer plug 28, one strut is in the chamber 48 and one strut is in the catheter 35. Having most all of the entire distance from one strut to the next in the introducer plug 28 facilitates reduction such that it is easier to introduce the next strut into the catheter shaft. Having the length of the tapered introducer plug 28 to be slightly less than a stent strut also allows forced transference of the stent from the aperture 48 of a crimping apparatus 14, into the introducer plug 28, without snagging a strut, and allows for the stent to have a slightly reduced outside diameter at the strut ends during entrance into the outer catheter shaft 35. The length of the introducer plug 28 is suitably about 0.001 inch to 1 inch (about 0.025 mm to about 25.4 mm), and more suitably about 0.025 inches to about 0.075 inches (about 0.635 mm to about 1.905 mm). In one embodiment, the length of the introducer plug is 0.050 inches (about 1.270 mm).

Many stents are formed having a node/strut structure. Having a stent introducer plug with a length less than one strut or less than the distance between nodes, as described above, can be advantageous in that the change in diameter is affected more in the nodes of a stent structure, than in the struts. For stents formed from shape memory alloys such as the nickel-titanium, i.e. nitinol, alloys, this may allow for the martensitic state to be introduced into each node specifically, resulting in a lower deployment force. In the martensitic state, the radial and frictional forces of the nitinol type of stents are reduced while in the austenitic state the radial and frictional forces are higher. When nitinol stents axe stressed, they go into the martensitic state. They may be stressed either by cooling, or by stress, or both.

Thus, the present method may allow stressing of the stents and thus entry into the martensitic state without cooling. Having the stents in a martensitic state thus allows for lower frictional, i.e. the radial force, and deployment forces, i.e. those required to push the stent out of the catheter shaft. This type of phenomenon is discussed in U.S. Pat. No. 6,306,141 which is incorporated by reference herein in its entirety.

The shaft 26 may be attached to a horizontally mounted hollow rod pneumatic cylinder 42. If employed in combination with a crimping system as described above, when the aperture 48 of the crimping apparatus 14 is open, the shaft 26 moves into the aperture 48 of the crimping apparatus 14. A stop (not shown) may be placed in the aperture that halts the travel of the intraluminal medical device or stent 25 within the aperture 48 and stops the stent from proceeding too far through the aperture. Once the stent is in the aperture 48 of the crimping apparatus 14, the stop is desirably removed. During crimping, the intraluminal medical device typically elongates along its axis as the diameter is reduced. If the stent is not allowed to elongate, the reduction in the diameter will not be uniform. Thus, the stop is removed. This may also prevent catching of the stent between the introducer plug 28 and the blades 22.

A forced air system designed to either heat or to chill the stent, for example, cryogenically, can also be used to transfer the stent through the system. The stent may be moved into the aperture 48 of the crimping, loading apparatus indicated generally at 14, 20 using a forced air system where it is transferred through a tube or some such structure. Forced air, rather than using a pushing device, will reduce the potential of damaging the stent by pushing it into the aperture 48 with an object. Using a triangular shaped introducer shaft as shown in FIG. 2, offers benefits when using such forced air. The triangular shaped introducer shaft 26 is shown within a circular lumen 27 of the introducer assembly 10 in FIG. 2. This configuration allows for air flow around the entire introducer shaft, thus providing better, more uniform heating and cooling of the entire shaft, and consequently better heating and cooling of the stent within the shaft.

Using a recirculating air system can prevent internal frost build-up in the system. A forced air system may be employed to transfer the stent through the system as well as for heating and cryogenically chilling the stent.

Figure 4:
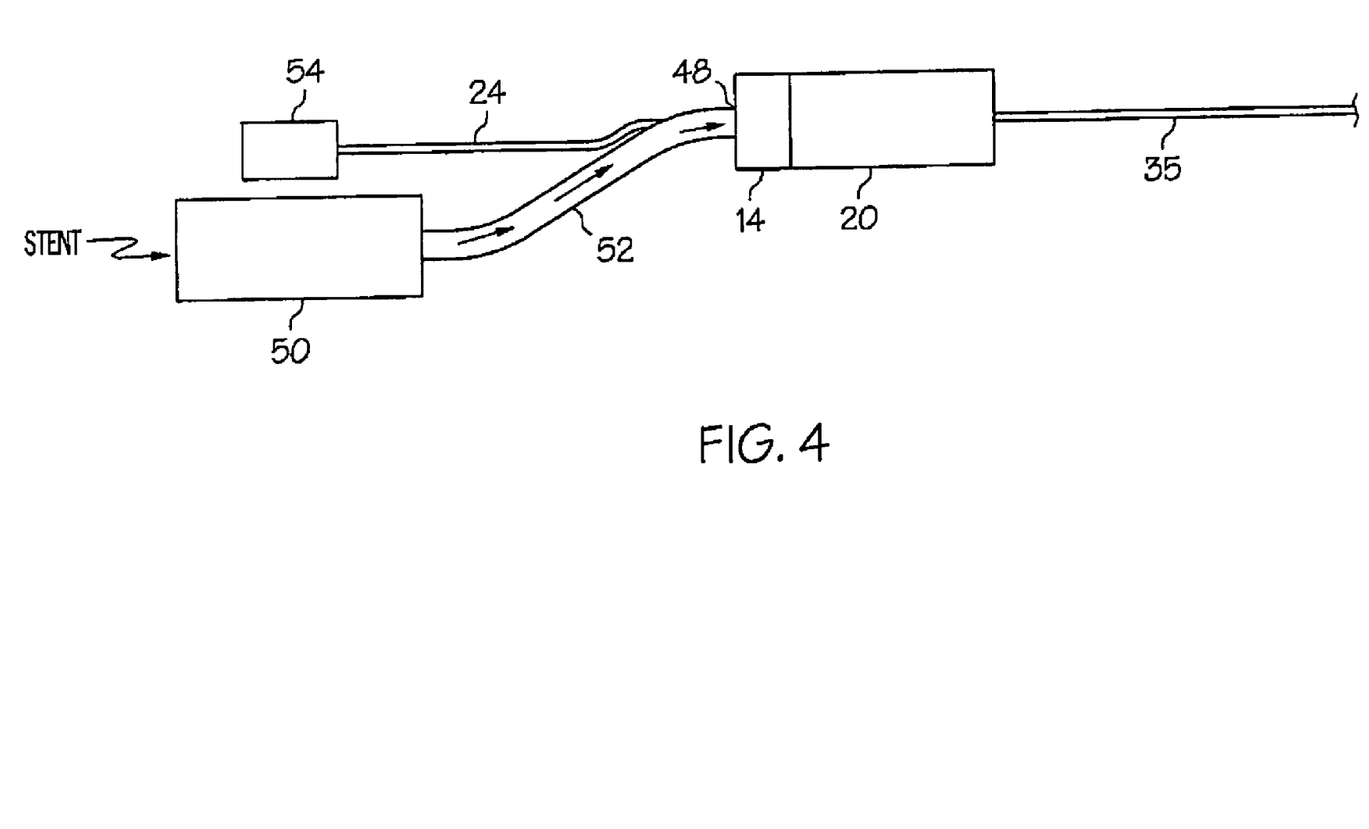
FIG. 4 is a simplistic flow diagram showing movement of a stent into a loading chamber through a transition tube and into the aperture of a crimping apparatus.

The stent may be placed in a loading chamber assembly 50 shown in FIG. 4 and released from the loading chamber using a stent pin. The stent is then moved from the loading chamber assembly 50, through the transition tube 52 and into the aperture 48 of the crimping/loading apparatus 14 and from there into a catheter tube 35. Forced air may be employed to move the stent from the loading chamber 50, through the transition tube 52 and into the aperture 48.

Once crimped, the stent is then moved through the plug lumen into the introducer shaft. As noted above, with a forced air system, an introducer shaft having a triangular external shape allows air to flow around the entire introducer shaft, allowing for better more uniform heating and cooling of the introducer shaft and thus better more uniform heating and cooling of the stents within the introducer shaft.

Optionally, cooling may take place in the loading chamber assembly 50 as well.

Desirably, the transition tube 52 through which the stent is moved from the loading chamber to the aperture 48 of the crimping apparatus is "s" shaped. This allows the pushing quill 24 to be aligned with the aperture of the crimping device such that the pushing quill 24 and the transition tube 52 do not interfere with one another. Pushing quill 24 may be actuated pneumatically or mechanically and is shown connected to an actuation device 54. The pushing quill 24 is employed to move the stent from the aperture of the crimping device and into the catheter shaft 35 once the diameter size of the stent has been reduced and crimping is thus complete. The pushing quill 24 is then retracted and another stent moved into the aperture 48 of the crimping apparatus 14. The next stent may then be placed in the loading chamber 50.

An operator may then slide the distal end of the outer catheter shaft from the product tray 46 into the introducer shaft 26 until it engages or comes into contact with the introducer plug 28 as shown in FIG. 3. A product hold cylinder and slip clamp 44 puts pressure onto the outer catheter shaft 35 as the horizontal air cylinder 40 retracts from the aperture 48 of the crimping apparatus. A die having a surface with a low coefficient of friction, such as by using a polytetraflouroethylene (PTFE), i.e. Teflon® die or Teflon® coating, can be beneficial. Furthermore, the die may be slightly smaller than the outer catheter shaft 35. This may further facilitate placing of the catheter shaft 35 over the ends 36 of the introducer plug 28. This action creates forced pressure onto the outer catheter shaft 35 allowing the introducer plug 28 to flare the ends of the outer catheter shaft 35. This flaring can help to prevent the nodes of the stent from catching on the outer catheter shaft 35 which can result in delamination of tube layers if the outer catheter shaft has a multilayer construction, for example.

Upon completion of the stent load, the quill 24 retracts, the aperture of the crimping device opens, and the introducer shaft extends into the aperture prepared for the next load.

The present inventive concepts may be employed in combination with any crimping apparatus. Such crimping apparatuses are known to those of skill in the art. For example, U.S. Pat. No. 6,360,577 B2, U.S. Pat. No. 6,568,235 B1 and U.S. Patent Application Publication No. US 2002/0138966 A1, are all examples of such crimping apparatuses, each document of which is incorporated by reference herein in its entirety. The present invention is not limited by the type of crimping apparatus which is employed.

Figure 5:
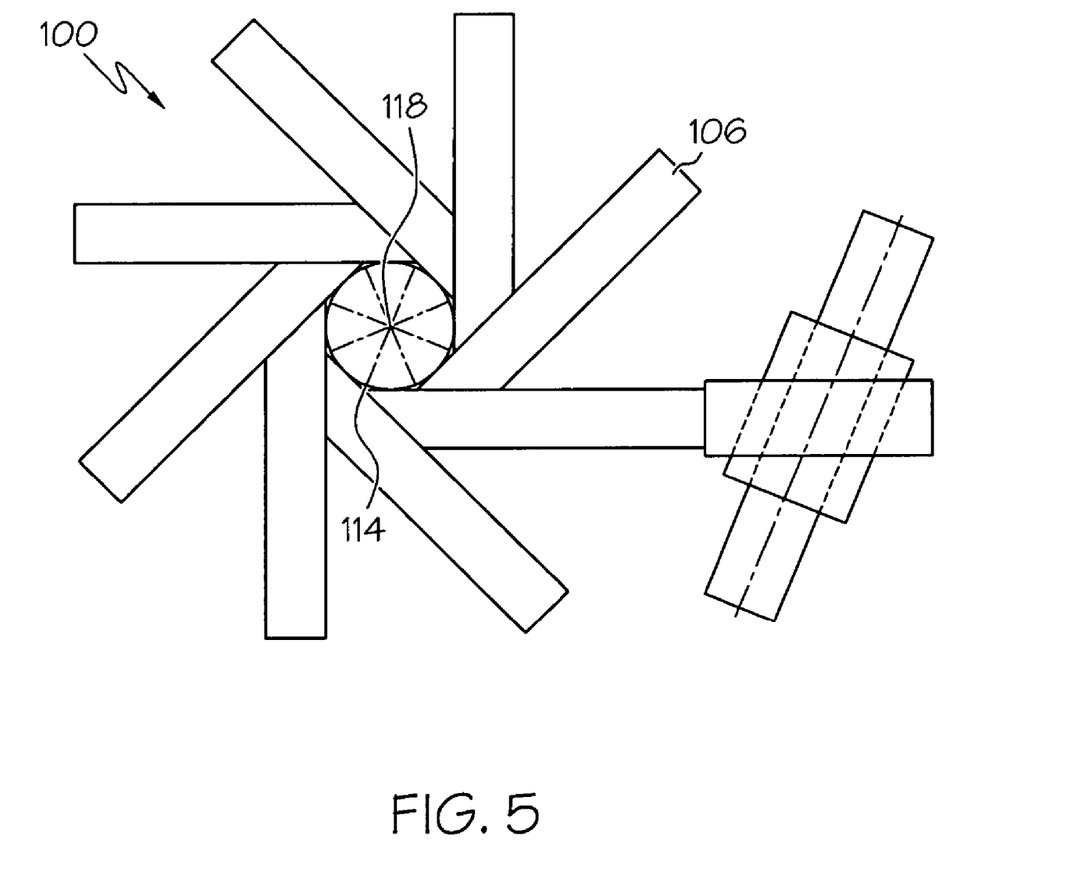
FIG. 5 shows an aperture of a type of crimping apparatus which may be used in combination with the present invention.

FIG. 5 is an example of one configuration of a crimping aperture/apparatus which may be used in accordance with the present invention. This crimping apparatus includes eight coupled movable blades 106 disposed about a reference circle 114 to form an aperture 118 whose size may be varied. Crimping apparatuses of this type are described in U.S. Pat. No. 6,360,577.

The apparatus may have as few as three blades, and as many as sixteen or more blades, limited only by how many blades may physically be coupled together, under the relevant size constraints. As the number of blades is increased, the profile of the aperture and hence of the medical device following reduction in size, becomes smoother.

Thus, a medical device may be manipulated using a device as described above by application of a radial inward force. The medical device is placed into the shrinkable aperture formed by the blades disposed about a reference circle and the blades are simultaneously moved inward to apply a radial inward force to the medical device.

Figure 6:
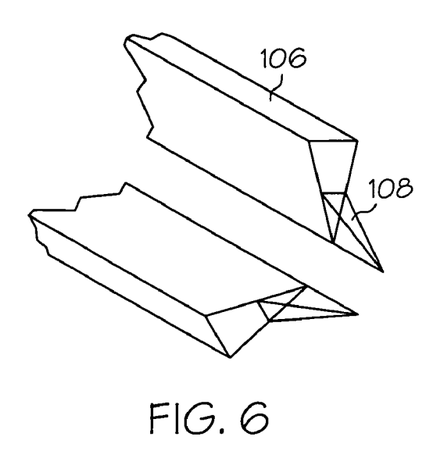
FIG. 6 illustrates blades for a crimping device having modular alignment structures on the blades.

The blades of such crimping apparatuses as those described above may be varied in order to provide improved alignment of the crimping apparatus with an introducing apparatus for loading an intraluminal medical device from the crimping apparatus and into an outer shaft of a catheter delivery assembly, for example. FIG. 6 illustrates blades having modular alignment structures 108 attached to the ends of the blades. These alignment structures are shown as conical flanges extending from the end of the blades. The alignment structures 108 may be formed from the same material as the blades 106, or from a different material than the blades 106. The alignment structures 108 may be attached using any means known in the art including usual fastening devices, as well as adhesively, for example. The modular nature of these structures allows for quick interchangeability if different sizes or structures are desired. Any number of the blades may be provided with such structures to improve alignment and facilitate loading of the intraluminal medical device into an outer shaft of a catheter delivery assembly without damage to the medical device or to the outer shaft.

Figure 7:
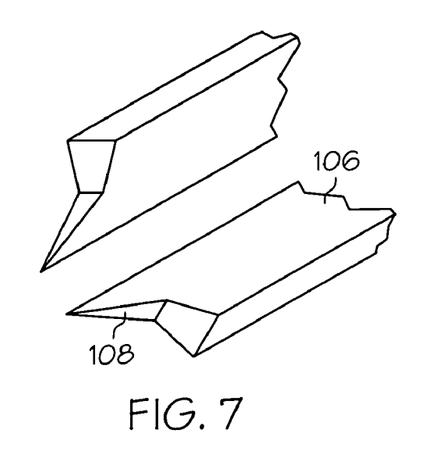
FIG. 7 illustrates blades for a crimping device having integral alignment structures on the blades.

FIG. 7 illustrates blades of a similar structure to those shown in FIG. 6. However, these conical flanges are integral with the blades. In such an embodiment, the blades are formed from the same material as the blades.

Figure 8:
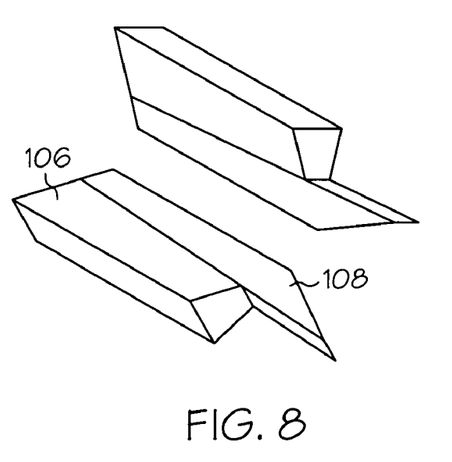
FIG. 8 illustrates blades for a crimping device having alternative modular alignment structures on the blades.

FIG. 8 illustrates blades 106 having alignment structures of a different configuration than those shown in FIG. 6. While these alignment structures 108 are also modular with the blades 106, as are the ones shown in FIG. 6, they are connected along the length of the blade 106 rather than at the edge.

Figure 9:
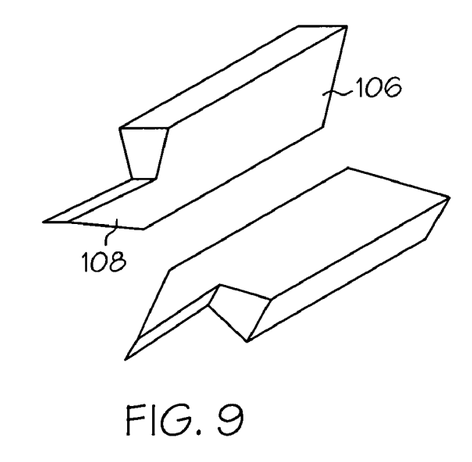
FIG. 9 illustrates blades for a crimping device having alternative integral alignment structures on the blades.

FIG. 9 illustrates alignment structures 108 similar in configuration to those shown in FIG. 8, but which are integral with the blades 106.

Figure 10:
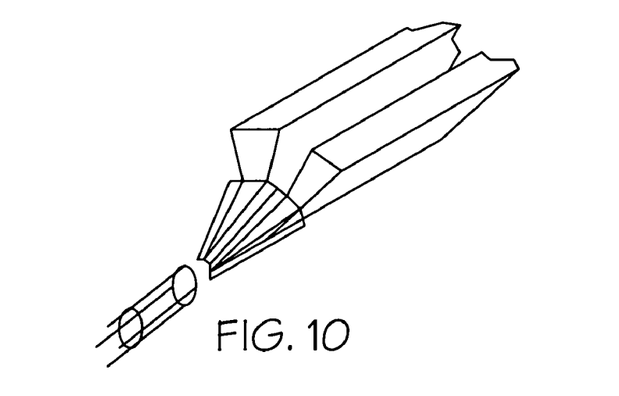
FIG. 10 is a partial view of a crimping apparatus having blades with integral alignment structures according to the invention shown in combination with a catheter shaft.

FIG. 10 is a partial view of a crimping apparatus according to the invention wherein blades 106 have integral alignment structures 108 shown in combination with a catheter shaft 35 with a flared end 34. Once crimping and loading is complete, the flare is cut from the catheter shaft.

The crimping apparatus and method of the present invention is adaptable with thermal capability to operate at temperatures ranging between 37° C. and 300° C. by placing heater cartridges in the segments through its back. The apparatus and methods are adaptable with cryogenic capability to operate at temperature ranging between −200° C. and −37° C. Liquid nitrogen may be used to cool the segments or to cool the housing plates. Thus, the apparatus and method are useful for those medical devices made from materials such as the shape memory nickel-titanium alloys. These alloys are often referred to in the industry as nitinol.

Such alloys undergo a transition between an austenitic state and a martensitic state at certain temperatures. When such alloys are deformed while in the martensitic state, the deformation is retained until they are heated to a transition temperature, at which time time they begin to revert to their original configuration as they start to transform to their austenitic state. As the temperature increases, the transition continues until the material is entirely in its austenitic phase and has reverted to its original configuration. The temperatures at which these transitions occur are affected by the nature of the alloy and the condition of the material. Nickel-titanium-based alloys (NiTi), for example, have a transition temperature which is slightly lower than body temperature. Thus, expandable, intraluminal medical devices formed from nickel-titanium alloys like nitinol, will revert to their austenitic state when implanted in a body.

Self-expanding stents formed from nitinol are deformed in the martensitic state for loading onto a constraining delivery system. The colder temperatures causes the crimped nitinol stent to stay at the reduced diameter. Additionally, it is believed that the colder temperatures make nitinol more malleable which reduces fatigue. The apparatuses described above can be advantageously employed for crimping and loading of intraluminal medical devices formed from such alloys.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A loading apparatus for loading a self-expanding stent into a catheter delivery system in combination with a crimping apparatus for reducing the diameter of said self-expanding stent from a first diameter to a second diameter prior to loading said self-expanding stent into said catheter delivery system, said crimping apparatus comprising at least three coupled, movable blades which form an aperture whose size may be varied, said loading apparatus having an alignment plug with a tapered portion for matingly engaging a tapered portion of an actuation hub of said crimping apparatus.

2. The loading apparatus of claim 1, wherein the mating engagement of said tapered portions provides for coaxial self-alignment between a lumen of the loading apparatus and a crimping chamber of said crimping apparatus.

3. An apparatus for loading a medical device into a catheter delivery system, the apparatus constructed and arranged to matingly engage a crimping apparatus having a crimping chamber for reducing the diameter of said medical device from a first diameter to a second diameter prior to loading said medical device into said catheter delivery system;
the apparatus comprising an introducer shaft having an internal lumen for receiving an outer catheter shaft of said catheter delivery system, the introducer shaft comprising an introducer plug having a lumen through which the medical device is introduced, wherein the lumen of said introducer plug tapers from an opening having a larger diameter at an opening of the introducer shaft to an opening having a smaller diameter for engaging said outer catheter shaft, and wherein the mating engagement between said apparatus and said crimping apparatus provides for coaxial self-alignment between said internal lumen and said crimping chamber.

4. The apparatus of claim 3 wherein said introducer plug has a length which is slightly less than the length of a stent strut.

5. The apparatus of claim 3 wherein said introducer plug is modular with said introducer shaft.

6. The apparatus of claim 3 wherein said introducer plug has conical flanged edges extending from said opening for engaging an outer catheter shaft.

7. The apparatus of claim 3 wherein said introducer plug has flat edges at said opening for engaging an outer catheter shaft within said introducer shaft.

8. The apparatus of claim 3, wherein said introducer shaft has an outer triangular configuration.

9. In combination, a crimping apparatus for reducing the diameter of a medical device from a first diameter to a second diameter and a loading apparatus for introducing said medical device into a catheter delivery system, the crimping apparatus comprising at least three coupled, movable blades which form an aperture whose size may be varied, the crimping apparatus comprising an internal taper constructed and arranged to matingly engage an external taper on the loading apparatus, said loading apparatus comprising a plug, the plug having the external taper.

10. The combination of claim 9, said crimping apparatus having an actuation hub, said actuation hub having the internal taper for matingly engaging a loading apparatus.

11. The combination of claim 10, said loading apparatus comprising a plug, the plug having the external taper for matingly engaging said actuation hub of said crimping apparatus.

12. In combination, a crimping apparatus for reducing the diameter of a medical device from a first diameter to a second diameter and a loading apparatus for introducing said medical device into a catheter delivery system, said crimping apparatus comprising at least three coupled, movable blades which form an aperture whose size may be varied, said crimping apparatus comprising a tapered portion constructed and arranged to matingly engage a complementary tapered portion of said loading apparatus.

13. The combination of claim 12 wherein said loading apparatus further comprises an introducer shaft.

14. The combination of claim 13 wherein said introducer shaft has an external triangular configuration.

15. The combination of claim 14, said introducer shaft further comprising an introducer plug.

16. The combination of claim 15 wherein said introducer plug has a length which is slightly less than the length of a stent strut.

17. The combination of claim 13, said introducer plug having a lumen tapering from a first opening having a larger diameter adjacent the opening of the introducer shaft through which a medical device is introduced and a second opening having a smaller diameter for engaging an outer catheter shaft within said introducer shaft.

18. The combination of claim 17 wherein said first opening has a diameter which is slightly larger than an aperture of a crimping apparatus which has been sized to receive a stent therein.

19. The combination of claim 17 wherein said second opening has a diameter which is slightly larger than the diameter of an outer catheter shaft.

20. An apparatus for reducing the diameter of a medical device from a first diameter to a second diameter and loading the medical device into a catheter, the apparatus comprising a crimping portion having at least three coupled, movable blades which form an aperture whose size may be varied and a tool for matingly engaging a loading portion of the apparatus, the loading portion having a tapered internal lumen.

21. The apparatus of claim 20 wherein said tool is a conical flange adjacent the edge of said at least one of said blades.

22. The apparatus of claim 20 wherein said tool is integral with at least one of said blades.

23. The apparatus of claim 20 wherein each of said blades has a tool which is integral with the blade.

24. The apparatus of claim 20 wherein said tool is modular to at least one of said blades.

25. The apparatus of claim 20 wherein each of said blades has a modular tool.

26. The apparatus of claim 20 wherein said tool is modular with all of said blades.

27. The apparatus of claim 20 wherein said at least one tool is attached to at least one of said blades mechanically.

28. The apparatus of claim 27 wherein said at least one tool is attached to at least one of said blades with a screw, thread, weld or adhesively.

29. The apparatus of claim 20 wherein said at least one tool is polymeric, metallic or a combination thereof.

30. The apparatus of claim 20 wherein said at least one tool is formed from the same material as said blades.

31. The apparatus of claim 20 wherein said at least one tool is formed from at least one polymeric material selected from the group consisting of polyolefins, polyamides, polyesters, polyurethanes, polyacetals, polycarbonate, copolymers thereof and mixtures thereof.

32. The apparatus of claim 31 wherein said at least one polymeric material is selected from the group consisting of nylon, polyethylene terephthalate, polybutylene terephthalate, acetal homopolymers, polyetherether ketone, and mixtures thereof.

33. The apparatus of claim 20 wherein said at least one tool is formed from at least one metal selected from the group consisting of copper, cobalt, stainless steel, steel, aluminum, and alloys thereof.

34. The apparatus of claim 33 further comprising a coating which reduces the coefficient of friction.

35. The apparatus of claim 34 wherein said coating comprises polytetrafluoroethylene.

36. The apparatus of claim 20 wherein said at least one tool is formed from ceramic.

37. The apparatus of claim 20 wherein said medical device is a stent.

38. An apparatus comprising a crimping portion for crimping a medical device and a loading portion for loading said medical device into a catheter, the crimping portion having at least three coupled, movable blades which form a crimping aperture, the crimping portion comprising a conical portion, the loading portion having an internal lumen, the loading portion comprising a complimentary conical portion the conical portion and complimentary conical portion constructed and arranged for coaxial self-alignment between the crimping aperture and the internal lumen.

* * * * *